United States Patent
Schelges et al.

(10) Patent No.: US 10,441,522 B2
(45) Date of Patent: Oct. 15, 2019

(54) SURFACTANT-CONTAINING CLEANING AGENT COMPOSITIONS WITH SPECIFIC COMBINATIONS OF FOUR PRESERVATIVES

(71) Applicant: Henkel AG & Co. KGaA, Duesseldorf (DE)

(72) Inventors: Heike Schelges, Willich (DE); Rainer Simmering, Grevenbroich (DE); Barbara Heide, Krefeld (DE); Melanie Rauschenberg, Kamen (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/372,145

(22) Filed: Dec. 7, 2016

(65) Prior Publication Data

US 2017/0165167 A1 Jun. 15, 2017

(30) Foreign Application Priority Data

Dec. 11, 2015 (DE) .......................... 10 2015 225006

(51) Int. Cl.
| | | |
|---|---|---|
| C11D 3/48 | (2006.01) |
| A61K 8/49 | (2006.01) |
| A61K 8/23 | (2006.01) |
| A61K 8/34 | (2006.01) |
| A61K 8/36 | (2006.01) |
| A61K 8/42 | (2006.01) |
| A61K 8/44 | (2006.01) |
| A61K 8/46 | (2006.01) |
| A61K 8/60 | (2006.01) |
| A61Q 19/10 | (2006.01) |
| A61Q 5/02 | (2006.01) |

(52) U.S. Cl.
CPC .............. *A61K 8/4953* (2013.01); *A61K 8/23* (2013.01); *A61K 8/34* (2013.01); *A61K 8/347* (2013.01); *A61K 8/36* (2013.01); *A61K 8/361* (2013.01); *A61K 8/42* (2013.01); *A61K 8/44* (2013.01); *A61K 8/442* (2013.01); *A61K 8/463* (2013.01); *A61K 8/4926* (2013.01); *A61K 8/602* (2013.01); *A61Q 5/02* (2013.01); *A61Q 19/10* (2013.01); *A61K 2800/524* (2013.01); *A61K 2800/592* (2013.01)

(58) Field of Classification Search
CPC ....................................................... C11D 3/48
See application file for complete search history.

(56) References Cited

U.S. PATENT DOCUMENTS

| | | | |
|---|---|---|---|
| 5,670,160 A | 9/1997 | Eggensperger et al. | |
| 2006/0115440 A1* | 6/2006 | Arata et al. ............ | A61K 8/365 424/65 |
| 2007/0248561 A1* | 10/2007 | Milbradt ................ | A61K 8/042 424/70.16 |
| 2009/0123577 A1* | 5/2009 | Beilfuss et al. ......... | A61K 8/30 424/729 |

FOREIGN PATENT DOCUMENTS

| | | |
|---|---|---|
| EP | 1414394 B1 | 6/2009 |
| WO | 03/043593 A1 | 5/2003 |
| WO | 2007/014580 A1 | 2/2007 |
| WO | 2012055855 A1 | 5/2012 |

OTHER PUBLICATIONS

GB Search Report GB1620947.0 Completed: Nov. 30, 2017; dated Dec. 1, 2017, 6 pages.

* cited by examiner

*Primary Examiner* — Charles I Boyer
(74) *Attorney, Agent, or Firm* — James J. Cummings

(57) ABSTRACT

Cleaning compositions include at least one specific preservative combination. The cleaning compositions are used for cleaning and/or caring for the skin and/or hair, and the specific preservative combination is used for the preservation of surfactant-containing cleaning compositions.

14 Claims, No Drawings

SURFACTANT-CONTAINING CLEANING AGENT COMPOSITIONS WITH SPECIFIC COMBINATIONS OF FOUR PRESERVATIVES

FIELD OF THE INVENTION

The present invention generally relates to cleaning agent compositions which, in addition to at least one surfactant, also include at least one specific preservative combination.

The present invention also relates to the use of cleaning compositions cleaning and caring for the skin and/or hair.

Lastly, the present invention relates to the use of preservative combinations for preserving surfactant-containing cleaning agent compositions.

BACKGROUND OF THE INVENTION

Due to their composition, cosmetic agents can be a culture medium for germs and microorganisms. These germs can lead on the one hand to a microbial contamination of the consumer, and on the other hand can modify ingredients of the cosmetics and thus form substances that have undesirable effects, such as sensitization or skin irritation. In order to prevent these undesirable effects and in order to ensure a certain minimum shelf life of the cosmetics, these must be preserved. Since preservatives in turn have the potential to cause irritation, their use in cosmetics is strictly regulated.

The skin microflora has a key influence on the different cosmetic parameters. Pathogenic germs, such as *Staphylococcus aureus* thus play a key role in the development of skin blemishes. The most recent studies also indicate that an unbalanced skin microflora can have an influence on skin ageing, since undesirable germs lead to an increased immune response of the skin, which in turn leads to increased inflammatory reactions, during the course of which skin ageing markers are stimulated.

It is therefore desirable to provide preservative compositions which on the one hand prevent the population of the product or the skin with undesirable germs and on the other hand do not or do not significantly interfere with the natural skin flora.

The mixing of various antimicrobial substances in order to increase the antimicrobial activity is known in principle. Document WO 03/043593 A1 proposes combining conventional antibacterial substances, such as triclosan, phenoxyethanol or hexetidine, with ethyl lauroyl arginate in order to increase the antimicrobial effect. In WO 2007/014580 A1, preservative mixtures are proposed which, in addition to ethyl lauroyl arginate, also include salts of organic or inorganic acids, sodium citrate, sodium acetate, sodium glutamate, sodium fumarate, sodium malate, sodium gluconate, sodium laurate, sodium lactate, sodium hexametaphosphate, sodium-tert-butyl-hydroquinone, sodium propylparabenate or the hydrochlorides of glucosamine or ethanolamine. Cosmetic compositions which include a preservative mixture formed from ethyl lauroyl arginate and parabenes, imidazolyl urea, phenoxyethanol, DMDM hydantoin, 2-methyl-5-chlor-3,4-isothiazolinone/2-methyl-3,4-isothiazolinone and Quaternium-15 are disclosed in EP 1414394 B1.

There is thus also a need to provide antimicrobial compositions which are highly effective in small use quantities.

To summarize, it is desirable to provide cleaning compositions which have an excellent cleaning and caring effect alongside good preservation. In particular, synergistic preservative mixtures should be discovered which are highly effective at low concentrations and which, on account of reduced use quantities on the whole, enable the preparation of cleaning compositions that cause little irritation and sensitization. Furthermore, no preservatives considered by consumers to be critical should be used. In addition, the foam quality, foam quantity and foam volume should not be negatively influenced by the addition of the preservative mixture.

Furthermore, other desirable features and characteristics of the present invention will become apparent from the subsequent detailed description of the invention and the appended claims, taken in conjunction with this background of the invention.

BRIEF SUMMARY OF THE INVENTION

A cleaning composition includes, in a cosmetically acceptable carrier, at least one surfactant, selected from the group of anionic surfactants, cationic surfactants, amphoteric surfactants, non-ionic surfactants, and mixtures thereof, and at least one preservative mixture, selected from the group of chloroxylenol and phenoxyisopropanol, undecylenic acid and formic acid, phenoxyisopropanol and piroctone olamine, phenoxyisopropanol and formic acid, sulfite(s) and hexetidine, ethyl lauroyl arginate and formic acid, ethyl lauroyl arginate and chloroxylenol, hexetidine and benzyl alcohol, hexetidine and chloroxylenol, hexetidine and piroctone olamine, hexetidine and chlorphenesin, hexetidine and formic acid, and mixtures thereof.

The at least one preservative mixture selected from the group of chloroxylenol and phenoxyisopropanol, undecylenic acid and formic acid, phenoxyisopropanol and piroctone olamine, phenoxyisopropanol and formic acid, sulfite(s) and hexetidine, ethyl lauroyl arginate and formic acid, ethyl lauroyl arginate and chloroxylenol, hexetidine and benzyl alcohol, hexetidine and chloroxylenol, hexetidine and piroctone olamine, hexetidine and chlorphenesin, hexetidine and formic acid, and mixtures thereof is used for the preservation of surfactant-containing cleaning compositions.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found, surprisingly, that the use of certain mixtures of preservatives in surfactant-containing cleaning compositions leads to a synergistic effect in relation to the preserving effect. The quantity of preservatives used can therefore be reduced without negatively influencing the preserving effect. Due to the reduced quantity of preservatives, the cleaning compositions according to the invention cause little irritation and sensitization. Furthermore, excellent preservation can be achieved by use of certain preservative mixtures, even without the use of preservatives found to be critical by consumers. Besides, the addition of the preservative mixtures also leads to an improved foam quality, foam quantity, and foam volume.

The subject of the present invention is a cleaning composition including, in a cosmetically acceptable carrier, a) at least one surfactant, selected from the group of anionic surfactants, cationic surfactants, amphoteric surfactants, non-ionic surfactants, and mixtures thereof, and b) at least one preservative mixture, selected from the group of
- chloroxylenol and phenoxyisopropanol
- undecylenic acid and formic acid
- phenoxyisopropanol and piroctone olamine
- phenoxyisopropanol and formic acid
- sulfite(s) and hexetidine
- ethyl lauroyl arginate and formic acid
- ethyl lauroyl arginate and chloroxylenol
- hexetidine and benzyl alcohol
- hexetidine and chloroxylenol
- hexetidine and piroctone olamine
- hexetidine and chlorphenesin
- hexetidine and formic acid and mixtures thereof.

The term "preservative mixture" is understood in accordance with the invention to mean a mixture of two of the aforementioned preservatives.

The term "% by weight" relates in the present case, unless otherwise specified, to the total weight of the cleaning composition according to the invention, wherein the sum of all ingredients of the agent according to the invention gives 100% by weight.

As first essential constituent a), the cleaning composition according to the invention includes at least one surfactant, selected from the group of anionic surfactants, cationic surfactants, amphoteric surfactants, non-ionic surfactants, and mixtures thereof.

The term "surfactant" is to be understood in accordance with the invention to mean amphiphilic (bifunctional) compounds consisting of at least one hydrophobic and at least one hydrophilic molecule part. The hydrophobic group is preferably a hydrocarbon chain having 8 to 28 carbon atoms, which can be saturated or unsaturated and linear or branched. This $C_8$-$C_{28}$ alkyl chain is particularly preferably linear.

Anionic surfactants are understood to mean surfactants which include exclusively anionic charges. Surfactants of this type preferably include at least one carboxyl group and/or sulfonic acid group and/or sulfate group. Within the scope of the present invention it has proven to be preferred when the cleaning compositions include at least one specific anionic surfactant. Preferred cleaning compositions of the present invention are therefore characterized in that the cosmetic agents include at least one anionic surfactant from the group of (i) alkyl(ether)sulfatene having 8 to 18 carbon atoms in the alkyl chain and 0 or 1 to 6 ethylene oxide units, (ii) $C_{12}$-$C_{18}$ alkylether carboxylates, (iii) $C_{12}$-$C_{18}$ acyl isethionates, (iv) $C_{12}$-$C_{18}$ acyl sarcosinates, (v) $C_{12}$-$C_{18}$ acyl taurines, and (vi) mixtures thereof.

Cationic surfactants are understood in accordance with the invention to mean surfactants having exclusively cationic charges. Surfactants of this type include at least one quaternary ammonium group. Specific cationic surfactants are preferably used in accordance with the invention. It is therefore advantageous within the scope of the present invention when they include at least one cationic surfactant from the group of (i) quaternized carboxylic acid triethanolamine ester salts, (ii) quaternized salts of carboxylic acids with diethanol alkylamines, (iii) quaternized salts of carboxylic acids with 1,2-dihydroxypropyldialkylamines, (iv) Quaternium-92, (v) $C_{10}$-$C_{22}$ alkyltrimethylammonium chlorides, and (vi) mixtures thereof.

The amphoteric surfactants are divided into ampholytic surfactants and zwitterionic surfactants. Ampholytic surfactants are understood to mean surface-active compounds that have both acidic (for example —COOH or —SO$_3$H groups) and alkaline hydrophilic groups (for example amino groups) and thus behave acidically or in an alkaline manner depending on the condition. Zwitterionic surfactants are understood by a person skilled in the art to mean surfactants which carry both a negative and a positive charge in the same molecule. The use of specific amphoteric surfactants has proven to be advantageous in accordance with the invention. Preferred cleaning compositions of the present invention are therefore characterized in that they include at least one amphoteric surfactant from the group of (i) $C_{10}$-$C_{18}$ alkyl betaines, (ii) $C_{8-12}$-alkylamido($C_1$-4)-alkyl betaines, (iii) $C_{10}$-$C_{18}$ alkyl sulfobetaines, (iv) $C_{10}$-$C_{18}$ alkyl amphoacetates and amphodiacetates, (v) $C_{10}$-$C_{18}$ alkylamphopropionates and dipropionates, and (vi) mixtures thereof.

Non-ionic surfactants are understood in accordance with the invention to mean surfactants which do not have any charged groups. Charged groups are to be understood to mean both permanently cationic and anionic groups and temporarily cationic and anionic groups. Permanently cationic and anionic groups have a cationic or anionic charge independent of the pH value. By contrast, temporarily cationic and anionic groups have a cationic or anionic charge only with certain pH values. It is preferred in accordance with the invention when the cleaning composition includes at least one non-ionic surfactant from the group of (i) $C_{10}$-$C_{18}$ alkyl polyglucosides, (ii) sorbitan esters and sorbitan ether esters, (iii) $C_{10}$-$C_{18}$ carboxylic acid monoethanol amides, (iv) $C_{10}$-$C_{18}$ alcohol ethoxylates with 2 to 40 mol ethylene oxide and/or propylene oxide per mol of alcohol, (v) $C_{10}$-$C_{18}$ amine oxides, (vi) glyceryl cocoates with 2 to 40 mol ethylene oxide and/or propylene oxide per mol of glyceryl cocoate, and (vii) mixtures thereof.

The at least one surfactant is advantageously used in the cleaning compositions according to the invention in certain quantity ranges. Preferred cleaning compositions of the present invention are therefore characterized in that they include—in relation to their total weight—0.5 to 60% by weight, preferably 1.0 to 50% by weight, preferably 1.5 to 40% by weight, in particular 2.0 to 30% by weight, of at least one surfactant selected from the group of anionic surfactants, cationic surfactants, amphoteric surfactants, non-ionic surfactants, and mixtures thereof. The use of the aforementioned quantities ensures a sufficient cleaning effect, foam quality, foam quantity, and foam volume. Furthermore, these quantities have no negative influence on the preserving effect of the preservative combination.

As second essential constituent b), the cleaning compositions according to the invention include at least one specific preservative mixture. These preservative mixtures have a synergistic effect in relation to the antimicrobial effect and thus lead to a particularly effective preservation of the cleaning compositions according to the invention. Furthermore, on account of the synergistic effect, the used quantity of said mixtures can be reduced, such that cleaning compositions which cause little irritation and sensitization are obtained. In addition, the foam quality, foam quantity, and the foam volume are improved by the use of the preservative mixture.

The cleaning compositions according to the invention preferably have a certain ratio by weight of the preservatives included in this cleaning composition. It is therefore preferred within the scope of the present invention when the cleaning composition has a ratio by weight of the first preservative to the second preservative in the preservative mixture b) of from 10:1 to 1:10, preferably from 8:1 to 1:8, preferably from 5:1 to 1:5, in particular from 2:1 to 1:2. The use of ratios by weight of this type has proven to be particularly advantageous in respect of the synergistic increase of the preservative power of this mixture.

The cleaning agent according to the invention includes the preservative mixture preferably in certain quantity ranges. Preferred cleaning compositions according to the invention are therefore characterized in that they include—in relation to their total weight—0.001 to 10% by weight, preferably 0.005 to 7.0% by weight, preferably 0.01 to 4.0% by weight, in particular 0.05 to 2.0% by weight, of at least one preservative mixture. The previously specified quantities relate to the total quantity of the preservative mixture, i.e. the mixture of the aforementioned two preservatives. The use of such amounts of the preservative mixture leads to excellent preservation of the cleaning compositions according to the invention. Furthermore, on account of the synergistic effect of the preservative mixture, the used amount thereof can be reduced without negatively influencing the preserving power. The cleaning compositions according to the invention therefore cause particularly little irritation and sensitization.

Particularly preferred preservative compositions R1 to R528 are specified in the Table on pages 6 to 16 of the priority document, DE 102015225006.7 filed Dec. 11, 2015, which is hereby incorporated by reference, (all values in % by weight, unless otherwise specified).

Instead of including the anionic, cationic, non-ionic or amphoteric surfactant, further particularly preferred embodiments of the cosmetic agents include a mixture of an aforementioned anionic and non-ionic surfactant or a mixture of an aforementioned non-ionic and cationic surfactant, or a mixture of an aforementioned non-ionic, cationic and amphoteric surfactant, or a mixture of an aforementioned anionic, non-ionic and amphoteric surfactant.

The aforementioned particularly preferred cleaning compositions, in particular the cleaning compositions R 1 to R 528, have an excellent cleaning effect and good preservation. Due to the synergistic effect of the used preservative mixture, the amount thereof can be reduced, without negatively influencing the preserving effect. The cleaning compositions according to the invention therefore cause little irritation and sensitization. Furthermore, due to the use of the aforementioned preservative mixture, the foam quality and the foam volume can be improved, such that the use of said mixture does not lead to a negative influence on the cleaning properties.

The preserving effect can be further increased when the cleaning composition additionally includes at least one further preservative selected from the group of benzyl alcohol(s), chloroxylenol, phenoxyisopropanol, undecylenic acid, formic acid, piroctone olamine, sulfite(s), hexetidine, ethyl lauroyl arginate, and chlorphenesin. The further preservative is selected here in such a way that it differs from the preservatives of the used preservative mixture.

Preferred cleaning compositions according to the invention are therefore characterized in that they additionally include at least one further preservative selected from the group of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 3 different preservatives.

Further preferred cleaning compositions according to the invention are characterized in that they additionally include at least two further preservatives, selected from the group of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 4 different preservatives.

Furthermore, cleaning compositions that are advantageous in accordance with the invention are those which additionally include at least three further preservatives, selected from the group of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 5 different preservatives.

In addition, cleaning compositions that are preferred within the scope of the present invention are those that additionally include at least four further preservatives, selected from the group of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 6 different preservatives.

Lastly, preferred cleaning compositions according to the invention are which additionally include at least six further preservatives, selected from the group of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 8 different preservatives.

In this context, it is advantageous when the at least one additional preservative is used in a specific total amount. It is therefore preferred in accordance with the invention when the cleaning composition includes—in relation to its total weight—0.1 to 10% by weight, preferably 0.1 to 7.0% by weight, preferably 0.1 to 4.0 by weight, in particular 0.1 to 6.0% by weight, of at least one additional preservative. If more than one additional preservative is used, the above-specified total amounts relate to the mixture of these preservatives. The use of such amounts of the at least one additional preservative leads to a further increase of the preserving power, without, however, causing incompatibilities with the further ingredients of the cleaning composition according to the invention.

Particularly preferred embodiments of the present invention are therefore characterized in that the embodiments R1 to R528 specified on pages 6 to 16 of the priority document additionally include at least one further, specific preservative. It is therefore particularly preferred when the embodiments R1 to R4, R49 to R52, R97 to R100, R145 to R148, R193 to R196, R241 to R244, R289 to R292, R337 to R340, R385 to R388, R433 to R436, and R481 to R484 specified on pages 6 to 16 of the priority document each include the following preservative or mixtures thereof PM1 to PM157 in a total amount of from 0.1 to 6.0% by weight—in relation to the total weight of the cleaning composition (u=undecylenic acid, a=formic acid, pi=piroctone olamine s=sulfite, h=hexetidine, e=ethyl lauroyl arginate*HCl, ch=chlorphenesin, b=benzyl alcohol)

| PM1 | PM2 | PM3 | PM4 | PM5 | PM5 | PM6 | PM7 |
|---|---|---|---|---|---|---|---|
| U | A | pi | s | h | e | ch | u + a |
| PM8 | PM9 | PM10 | PM11 | PM12 | PM13 | PM14 | PM15 |
| u + a + pi | u + a + pi + s$^{1)}$ | u + a + pi + s$^{1)}$ + h | u + a + pi + s$^{1)}$ + h + e | u + a + pi + s$^{1)}$ + h + e + ch | u + a + s$^{1)}$ | u + a + s$^{1)}$ + h | u + a + s$^{1)}$ + h + e |
| PM16 | PM17 | PM18 | PM19 | PM20 | PM21 | PM22 | PM23 |
| u + a + s$^{1)}$ + h + e + ch | u + a + h | u + a + h + e | u + a + h + e + ch | u + a + e | u + a + e + ch | u + a + ch | u + pi |
| PM24 | PM25 | PM26 | PM27 | PM28 | PM29 | PM30 | PM31 |
| u + pi + s$^{1)}$ | u + pi + s$^{1)}$ + h | u + pi + s$^{1)}$ + h + e | u + pi + s$^{1)}$ + h + e + ch | u + pi + h | u + pi + h + e | u + pi + h + e + ch | u + pi + e |
| PM32 | PM33 | PM34 | PM35 | PM36 | PM37 | PM38 | PM39 |
| u + pi + e + ch | u + pi + ch | u + s$^{1)}$ | u + s$^{1)}$ + h | u + s$^{1)}$ + h + e | u + s$^{1)}$ + h + e + ch | u + s$^{1)}$ + e | u + s$^{1)}$ + e + ch |
| PM40 | PM41 | PM42 | PM43 | PM44 | PM45 | PM46 | PM47 |
| u + s$^{1)}$ + ch | u + h | u + h + e | u + h + e + ch | u + h + ch | u + e | u + e + ch | u + ch |
| PM48 | PM49 | PM50 | PM51 | PM52 | PM53 | PM54 | PM55 |
| a + pi | a + pi + s | a + pi + s$^{1)}$ + h | a + pi + s$^{1)}$ + h + e | a + pi + s$^{1)}$ + h + e + ch | a + pi + h | a + pi + h + e | a + pi + h + e + ch |
| PM56 | PM57 | PM58 | PM59 | PM60 | PM61 | PM62 | PM63 |
| a + pi + e | a + pi + e + ch | a + pi + ch | a + s$^{1)}$ | a + s$^{1)}$ + h | a + s$^{1)}$ + h + e | a + s$^{1)}$ + h + e + ch | a + s$^{1)}$ + e |
| PM64 | PM65 | PM66 | PM67 | PM68 | PM69 | PM70 | PM71 |
| a + s$^{1)}$ + e + ch | a + s$^{1)}$ + ch | a + h | a + h + e | a + h + e + ch | a + h + ch | a + e | a + e + ch |
| PM72 | PM73 | PM74 | PM75 | PM76 | PM78 | PM79 | PM80 |
| a + ch | pi + s$^{1)}$ | pi + s$^{1)}$ + h | pi + s$^{1)}$ + h + e | pi + s$^{1)}$ + h + e + ch | pi + s$^{1)}$ + e | pi + s$^{1)}$ + e + ch | pi + s$^{1)}$ + ch |
| PM81 | PM82 | PM83 | PM84 | PM85 | PM86 | PM87 | PM88 |
| pi + h | pi + h + e | pi + h + e + ch | pi + h + ch | pi + e | pi + e + ch | pi + ch | s$^{1)}$ + h |
| PM89 | PM90 | PM91 | PM92 | PM93 | PM94 | PM95 | PM96 |
| s$^{1)}$ + h + e | s$^{1)}$ + h + e + ch | s$^{1)}$ + h + ch | s$^{1)}$ + e | s$^{1)}$ + e + ch | s$^{1)}$ + ch | h + e | h + e + ch |
| PM97 | PM98 | PM99 | PM100 | PM101 | PM102 | PM103 | PM104 |
| h + ch | e + ch | u + a + b | u + a + ch + b | u + a + e + ch + b | u + a + h + e + ch + b | u + a + s$^{1)}$ + h + e + ch + b | u + a + pi + s$^{1)}$ + h + e + ch + b |
| PM105 | PM106 | PM107 | PM108 | PM109 | PM110 | PM111 | PM112 |
| B | u + pi + b | u + pi + ch + b | u + pi + e + ch + b | u + pi + h + e + ch + b | u + pi + s$^{1)}$ + h + e + ch + b | u + s$^{1)}$ + b | u + s$^{1)}$ + ch + b |
| PM113 | PM114 | PM115 | PM116 | PM117 | PM118 | PM119 | PM120 |
| u + s$^{1)}$ + e + ch + b | u + s$^{1)}$ + h + e + ch + b | u + h + b | u + h + ch + b | u + h + e + ch + b | u + b | u + ch + b | u + e + ch + b |
| PM121 | PM122 | PM123 | PM124 | PM125 | PM126 | PM127 | PM128 |
| a + pi + b | a + pi + ch + b | a + pi + e + ch + b | a + pi + h + e + ch + b | a + pi + s$^{1)}$ + h + e + ch + b | a + s$^{1)}$ + b | a + s$^{1)}$ + ch + b | a + s$^{1)}$ + e + ch + b |

-continued

| PM129 | PM130 | PM131 | PM132 | PM133 | PM134 | PM135 | PM136 |
|---|---|---|---|---|---|---|---|
| a + s[1]) + h + e + ch + b | a + h + b | a + h + ch + b | a + h + e + ch + b | a + b | a + ch + b | a + e + ch + b | pi + s[1]) + b |

| PM137 | PM138 | PM139 | PM140 | PM141 | PM142 | PM143 | PM144 |
|---|---|---|---|---|---|---|---|
| pi + s[1]) + ch + b | pi + s[1]) + e + ch + b | pi + s[1]) + h + e + ch + b | pi + h + b | pi + h + ch + b | pi + h + e + ch + b | pi + b | pi + ch + b |

| PM145 | PM146 | PM147 | PM148 | PM149 | PM150 | PM151 | PM152 |
|---|---|---|---|---|---|---|---|
| pi + e + ch + b | s[1]) + h + b | s[1]) + h + ch + b | s[1]) + h + e + ch + b | s[1]) + b | s[1]) + ch + b | s[1]) + e + ch + b | h + b |

| PM153 | PM154 | PM155 | PM156 | PM157 | | | |
|---|---|---|---|---|---|---|---|
| h + ch + b | h + e + ch + b | e + b | e + ch + b | ch + b | | | |

[1]) Sulfite is selected from the group of sodium sulfite, ammonium bisulfite, ammonium sulfite, potassium sulfite, potassium hydrogen sulfite, sodium bisulfite, sodium metabisulfite, and potassium metabisulfite, and mixtures thereof.

In addition, particularly preferred embodiments of the present invention are characterized in that the aforementioned cleaning compositions R5 to R8, R53 to R56, R101 to R104, R149 to R152, R197 to R200, R245 to R248, R293 to R296, R341 to R344, R389 to R392, R437 to R440, and R485 to R488 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 u=undecylenic acid is replaced by c=chloroxylenol and a=formic acid is replaced by p=phenoxyisopropanol.

Furthermore, compositions that are preferred within the scope of the present invention are those in which the aforementioned cleaning compositions R9 to R12, R57 to R60, R105 to R108, R153 to R156, R201 to R204, R249 to R252, R297 to R300, R345 to R348, R393 to R396, R441 to R444, and R489 to R492 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 pi=piroctone olamine is replaced by c=chloroxylenol.

In addition, compositions that are preferred within the scope of the present invention are those in which the aforementioned cleaning compositions R13 to R16, R61 to R64, R109 to R112, R157 to R160, R205 to R208, R253 to R256, R301 to R304, R349 to R352, R397 to R400, R445 to R448 and R493 to R496 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 a=formic acid is replaced by c=chloroxylenol.

Furthermore, compositions that are preferred within the scope of the present invention are those in which the aforementioned cleaning compositions R17 to R20, R65 to R68, R113 to R116, R161 to R164, R209 to R212, R257 to R260, R305 to R308, R353 to R356, R401 to R404, R449 to R452 and R497 to R500 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 s=sulfite is replaced by c=chloroxylenol and h=hexetidine is replaced by p=phenoxyisopropanol.

It is also advantageous within the scope of the present invention when the aforementioned cleaning compositions R21 to R24, R69 to R72, R117 to R120, R165 to R168, R213 to R216, R261 to R264, R309 to R312, R357 to R360, R405 to R408, R453 to R456, and R501 to R504 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 e=ethyl lauroyl arginate*HCl is replaced by c=chloroxylenol and a=formic acid is replaced by p=phenoxyisopropanol.

Furthermore, it is advantageous within the scope of the present invention when the aforementioned cleaning compositions R25 to R28, R73 to R76, R121 to R124, R169 to R172, R217 to R220, R265 to R268, R313 to R316, R361 to R364, R409 to R412, R457 to R460, and R505 to R508 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 e=ethyl lauroyl arginate*HCl is replaced by p=phenoxyethanol.

In addition, it is advantageous within the scope of the present invention when the aforementioned cleaning compositions R29 to R32, R77 to R80, R125 to R128, R173 to R176, R221 to R224, R269 to R272, R317 to R320, R365 to R368, R413 to R416, R461 to R464 and R509 to R512 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 h=hexetidine is replaced by p=phenoxyethanol and b=benzyl alcohol is replaced by p=phenoxyisopropanol.

Furthermore, particularly preferred embodiments of the present invention are characterized in that the aforementioned cleaning compositions R33 to R36, R81 to R84, R129 to R132, R177 to R180, R225 to R228, R273 to R276, R321 to R324, R369 to R372, R417 to R420, R465 to R468, and R513 to R516 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 h=hexetidine is replaced by p=phenoxyisopropanol.

Furthermore, compositions that are preferred within the scope of the present invention are those in which the aforementioned cleaning compositions R37 to R40, R85 to R88, R133 to R136, R181 to R184, R229 to R232, R277 to R280, R325 to R328, R373 to R376, R421 to R424, R469 to R472, and R517 to R520 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 h=hexetidine is replaced by c=chloroxylenol and pi=piroctone olamine is replaced by p=phenoxyisopropanol.

In addition, compositions that are preferred within the scope of the present invention are those in which the aforementioned cleaning compositions R41 to R44, R89 to R92, R137 to R140, R185 to R188, R233 to R236, R281 to R284, R329 to R332, R377 to R380, R425 to R428, R473 to R476, and R521 to R524 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 h=hexetidine is replaced by p=phenoxyisopropanol.

Lastly, compositions that are preferred within the scope of the present invention are those in which the aforementioned cleaning compositions R45 to R48, R93 to R96, R141 to R144, R189 to R192, R237 to R240, R285 to R288, R333 to R336, R381 to R384, R429 to R432, R477 to R480, and R525 to R528 each additionally include the above-mentioned preservative or mixtures thereof PM1 to PM157 in a total amount of from 0.1 to 6.0% by weight—in relation to the total weight of the cleaning composition—with the provision that in the aforementioned PM1 to PM157 h=hexetidine is replaced by p=phenoxyisopropanol and a=formic acid is replaced by c=chloroxylenol.

The addition of the at least one further preservative leads to a further increase of the preserving power. In addition, the foam quality and stability is not negatively influenced and can even be improved by the addition of the at least one additional preservative.

Besides the components a) and b), which are compulsory in accordance with the invention, and the at least one further preservative, all further components known to a person skilled in the art for such cosmetic compositions can also be used, in principle, in the cleaning compositions according to the invention. Further active substances, auxiliaries and additives are, for example:

- thickening agents such as gelatins or plant gums, for example agar-agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, fully synthetic hydrocolloids such as polyvinyl alcohol,
- structurants, such as maleic acid and lactic acid,
- solvents and solubilizing agents, such as ethanol, isopropanol, ethylene glycol, propylene glycol, glycerol, and diethylene glycol,
- fiber structure-improving active substances, in particular mono-, di- and oligosaccharides, such as glucose, galactose, fructose, fruit sugar, and lactose,
- dyes for coloring the agent,
- substances for adjusting the pH value, such as α- and β-hydroxycarboxylic acids,
- active substances such as allantoin and bisabolol,
- complexing agents, such as EDTA, NTA, β-alanine diacetic acid and phosphonic acids,
- ceramides. Ceramides are understood to mean N-acyl-sphingosine (fatty acid amides of sphingosine) or synthetic analogues such as lipids (what are known as pseudo ceramides),
- opacifiers, such as latex, styrene/PVP copolymers and styrene/acrylamide copolymers,
- pearlescent agents, such as ethylene glycol mono- and distearate and PEG-3 distearate,
- pigments,
- propellants, such as propane-butane mixtures, $N_2O$, dimethylether, $CO_2$ and air,
- viscosity regulators such as salts (NaCl),
- cationic, non-ionic and amphoteric polymers,
- vitamins, in particular from the groups A, B, C, E, F and H,
- UV filters, in particular benzophenones, p-aminobenzoic acid esters, diphenyl acrylic acid esters, cinnamic acid esters, salicylic acid esters, benzimidazoles, and o-aminobenzoic acid esters,
- protein hydrolyzates and cationized protein hydrolyzates,
- humectants or penetration aids and/or swelling agents, in particular urea and urea derivatives, guanidine and derivatives thereof, arginine and derivatives thereof, water glass, imidazole and derivatives thereof, histidine and derivatives thereof, benzyl alcohol, glycol ether, propylene glycol ether, for example propylene glycol monoethyl ether, carbonates, hydrogen carbonates, 1,2-diols, and 1,3-diols,
- plant extracts, for example from green tea, white tea, oak bark, stinging nettle, *hamamelis*, hops, henna, camomile, burdock root, field horsetail, hawthorn, linden flowers, lychee, almonds, aloe vera, spruce needles, horse chestnut, sandal wood, juniper, coconut, mango, apricot, lime, wheat, kiwi, melon, orange, grapefruit, sage, rosemary, birch, malva, lady's smock, broad-leaved thyme, common yarrow, thyme, lemon balm, rest-harrow, coltsfoot, marshmallow, *ginseng*, ginger root, *echinacea purpurea*, olive, boerhavia *diffusa* root, fennel and celery,
- silicone oils, in particular polyalkyl siloxanes, polyaryl siloxanes, and polyalkylaryl siloxanes, which optionally can be functionalized with organic groups and/or ethoxy and/or propoxy groups.

The aforementioned further ingredients can be included—in relation to the total weight of the cleaning composition—in a total amount of from 0.001 to 50% by weight, preferentially from 0.01 to 40% by weight, preferably from 0.1 to 30% by weight, in particular from 0.5 to 20% by weight.

A second subject of the present invention is the use of a cleaning composition according to the invention for cleaning and caring for skin and hair.

That which has been said in respect of the cleaning compositions according to the invention applies, mutatis mutandis, with regard to further preferred embodiments of the method according to the invention, in particular with regard to the cleaning compositions used there.

Lastly, a third subject of the present invention is the use of at least one preservative mixture selected from the group of chloroxylenol and phenoxyisopropanol, undecylenic acid and formic acid, phenoxyisopropanol and piroctone olamine, phenoxyisopropanol and formic acid, sulfite(s) and hexetidine, ethyl lauroyl arginate and formic acid, ethyl lauroyl arginate and chloroxylenol, hexetidine and benzyl alcohol, hexetidine and chloroxylenol, hexetidine and piroctone olamine, hexetidine and chlorphenesin, hexetidine and formic acid, and mixtures thereof for the preservation of surfactant-containing cleaning compositions.

The use of the aforementioned preservative combinations leads to excellent preservation of surfactant-containing cleaning compositions. Due to the synergistic effect of these combinations in respect of the preserving effect, the amount of preservatives can be reduced, such that cleaning compositions that cause little irritation and sensitization are provided. In addition, the foam quality, foam quantity and foam volume are improved by the use of the aforementioned preservative mixtures. Here, surfactant-containing cleaning compositions are understood to mean compositions which include at least one surfactant and which are suitable for cleaning the skin and/or hair.

In this composition it can also be preferred to use an additional preservative in addition to the at least one preservative mixture. In particular, the preservatives or mixtures thereof PM1 to PM157 described in conjunction with the first subject of the invention are preferred.

That said in respect of the cleaning composition according to the invention also applies, mutatis mutandis, with regard to further embodiments of the use according to the invention.

The following examples explain the present invention, but are not intended to limit it.

Examples

The cleaning compositions specified below were prepared:

Shower gel (values in % by weight)

| Raw material | 1. | 1.2 | 1.3 | 1.4 | 1.5 | 1.6 |
|---|---|---|---|---|---|---|
| Sodium Laureth Sulfate | 9.50 | 9.50 | 9.50 | 9.50 | 9.50 | 9.50 |
| Disodium Cocoamphodiacetate | 1.56 | 1.56 | 1.56 | 1.56 | 1.56 | 1.56 |
| Cocamidopropyl Betaine | 1.52 | 1.52 | 1.52 | 1.52 | 1.52 | 1.52 |
| Sodium Chloride | 1.38 | 1.38 | 1.38 | 1.38 | 1.38 | 1.38 |
| Fragrance | 0.62 | 0.62 | 0.62 | 0.62 | 0.62 | 0.62 |
| Glycol Distearate | 0.45 | 0.45 | 0.45 | 0.45 | 0.45 | 0.45 |
| Citric Acid | 0.37 | 0.37 | 0.37 | 0.37 | 0.37 | 0.37 |
| PEG-7 Glyceryl Cocoate | 0.30 | 0.30 | 0.30 | 0.30 | 0.30 | 0.30 |
| Cocamide MEA | 0.23 | 0.23 | 0.23 | 0.23 | 0.23 | 0.23 |
| Chloroxylenol | 0.50 | — | — | — | — | 0.50 |
| Ethyl Lauroyl Arginate*HCl | 0.40 | — | — | — | — | 0.40 |
| Sodium Sulfite | — | 0.20 | — | — | — | 0.20 |
| Hexetidine | — | 0.10 | — | — | — | 0.10 |
| Formic acid | — | — | 0.50 | — | — | 0.50 |
| Phenoxyisopropanol | — | — | 1.00 | — | — | 1.00 |
| Undecylenic acid | — | — | — | — | — | 0.20 |
| Piroctone Olamine | — | — | — | — | — | 0.50 |
| Benzyl Alcohol | — | — | — | — | — | 1.00 |
| Chlorphenesin | — | — | — | — | — | 0.30 |
| PM [1) | — | — | — | 0.5 | 2.0 | — |
| PEG-40 Hydrogenated Castor Oil | 0.20 | 0.20 | 0.20 | 0.20 | 0.20 | 0.20 |
| Polyquaternium-7 | 0.14 | 0.14 | 0.14 | 0.14 | 0.14 | 0.14 |
| Laureth-10 | 0.09 | 0.09 | 0.09 | 0.09 | 0.09 | 0.09 |
| Laureth-2 | 0.05 | 0.05 | 0.05 | 0.05 | 0.05 | 0.05 |
| Propylene Glycol | 0.02 | 0.02 | 0.02 | 0.02 | 0.02 | 0.02 |
| PEG-55 Propylene Glycol Oleate | 0.02 | 0.02 | 0.02 | 0.02 | 0.02 | 0.02 |
| Niacinamide | 0.01 | 0.01 | 0.01 | 0.01 | 0.01 | 0.01 |
| CI 17200 | 0.00 | 0.00 | 0.00 | 0.00 | 0.00 | 0.00 |
| CI 42090 | 0.00 | 0.00 | 0.00 | 0.00 | 0.00 | 0.00 |
| Water | to 100 | to 100 | to 100 | to 100 | to 100 | to 100 |

[1) Preservative mixture, selected from one of the previously specified preservative mixtures PM1 to PM157

Liquid soap (values in % by weight)

| Raw material | 2.1 | 2.2 | 2.3 | 2.4 | 2.5 | 2.6 |
|---|---|---|---|---|---|---|
| Sodium Laureth Sulfate | 5.60 | 5.60 | 5.60 | 5.60 | 5.60 | 5.60 |
| Cocamidopropyl Betaine | 3.80 | 3.80 | 3.80 | 3.80 | 3.80 | 3.80 |
| Glycerin | 1.19 | 1.19 | 1.19 | 1.19 | 1.19 | 1.19 |
| Sodium Chloride | 0.90 | 0.90 | 0.90 | 0.90 | 0.90 | 0.90 |
| Fragrance | 0.67 | 0.67 | 0.67 | 0.67 | 0.67 | 0.67 |
| PEG-7 Glyceryl Cocoate | 0.30 | 0.30 | 0.30 | 0.30 | 0.30 | 0.30 |
| Styrene/Acrylates Copolymer | 0.30 | 0.30 | 0.30 | 0.30 | 0.30 | 0.30 |
| Citric Acid | 0.23 | 0.23 | 0.23 | 0.23 | 0.23 | 0.23 |
| Ethyl Lauroyl Arginate*HCl | 0.40 | — | — | — | — | 0.40 |
| Piroctone Olamine | 1.00 | — | — | — | — | 1.00 |
| Sodium Sulfite | — | — | — | — | — | 0.20 |
| Hexetidine | — | — | — | — | — | 0.10 |
| Formic acid | — | — | 0.50 | — | — | 0.50 |
| Phenoxyisopropanol | — | 1.00 | — | — | — | 1.00 |
| Undecylenic acid | — | — | 0.20 | — | — | 0.20 |
| Chloroxylenol | — | 0.50 | — | — | — | 0.50 |
| Benzyl Alcohol | — | — | — | — | — | 1.00 |

-continued

| Raw material | 2.1 | 2.2 | 2.3 | 2.4 | 2.5 | 2.6 |
|---|---|---|---|---|---|---|
| Chlorphenesin | — | — | — | — | — | 0.30 |
| PM [1] | — | — | — | 0.5 | 2.0 | — |
| Yogurt | 0.05 | 0.05 | 0.05 | 0.05 | 0.05 | 0.05 |
| Laureth-2 | 0.05 | 0.05 | 0.05 | 0.05 | 0.05 | 0.05 |
| Hexyl Salicylate | 0.03 | 0.03 | 0.03 | 0.03 | 0.03 | 0.03 |
| Propylene Glycol | 0.02 | 0.02 | 0.02 | 0.02 | 0.02 | 0.02 |
| PEG-55 Propylene Glycol Oleate | 0.02 | 0.02 | 0.02 | 0.02 | 0.02 | 0.02 |
| Niacinamide | 0.01 | 0.01 | 0.01 | 0.01 | 0.01 | 0.01 |
| Aloe Barbadensis Leaf Juice | 0.01 | 0.01 | 0.01 | 0.01 | 0.01 | 0.01 |
| Water | to 100 | to 100 | to 100 | to 100 | to 100 | to 100 |

[1] Preservative mixture, selected from one of the previously specified preservative mixtures PM1 to PM157

Washing gel (values in % by weight)

| Raw material | 3.1 | 3.2 | 3.3 | 3.4 | 3.5 | 3.6 |
|---|---|---|---|---|---|---|
| Cocamidopropyl Betaine | 5.70 | 5.70 | 5.70 | 5.70 | 5.70 | 5.70 |
| Caprylyl/Capryl Glucoside | 3.18 | 3.18 | 3.18 | 3.18 | 3.18 | 3.18 |
| Decyl Glucoside | 2.65 | 2.65 | 2.65 | 2.65 | 2.65 | 2.65 |
| Dehydroxanthan Gum | 1.19 | 1.19 | 1.19 | 1.19 | 1.19 | 1.19 |
| Sodium Chloride | 1.05 | 1.05 | 1.05 | 1.05 | 1.05 | 1.05 |
| Sodium PCA | 0.50 | 0.50 | 0.50 | 0.50 | 0.50 | 0.50 |
| Tilia Platyphyllos Flower Water | 0.50 | 0.50 | 0.50 | 0.50 | 0.50 | 0.50 |
| Citric Acid | 0.48 | 0.48 | 0.48 | 0.48 | 0.48 | 0.48 |
| Ethyl Lauroyl Arginate*HCl | 0.40 | — | 0.40 | — | — | 0.40 |
| Piroctone Olamine | — | 1.00 | — | — | — | 1.00 |
| Sodium Sulfite | — | — | — | — | — | 0.20 |
| Hexetidine | — | — | — | — | — | 0.10 |
| Formic acid | 0.50 | — | 0.50 | 0.50 | — | 0.50 |
| Phenoxyisopropanol | — | 1.00 | — | — | 1.00 | 1.00 |
| Undecylenic acid | — | — | — | 0.20 | — | 0.20 |
| Chloroxylenol | — | — | — | — | 0.50 | 0.50 |
| Benzyl Alcohol | — | — | — | — | — | 1.00 |
| Chlorphenesin | — | — | — | — | — | 0.30 |
| PM [1] | — | — | — | 0.2 | 1.5 | — |
| Glycerin | 0.10 | 0.10 | 0.10 | 0.10 | 0.10 | 0.10 |
| Fragrance | 0.10 | 0.10 | 0.10 | 0.10 | 0.10 | 0.10 |
| Citric Acid | 0.01 | 0.01 | 0.01 | 0.01 | 0.01 | 0.01 |
| Vitis Vinifera Bud Extract | 0.00 | 0.00 | 0.00 | 0.00 | 0.00 | 0.00 |
| Water | ad 100 | ad 100 | ad 100 | ad 100 | ad 100 | ad 100 |

[1] Preservative mixture, selected from one of the previously specified preservative mixtures PM1 to PM157

Washing gel (values in % by weight)

| Raw material | 4.1 | 4.2 | 4.3 | 4.4 | 4.5 | 4.6 |
|---|---|---|---|---|---|---|
| Hexanediol | 5.00 | 5.00 | 5.00 | 5.00 | 5.00 | 5.00 |
| Glycerin | 4.98 | 4.98 | 4.98 | 4.98 | 4.98 | 4.98 |
| Arachidyl Alcohol | 2.75 | 2.75 | 2.75 | 2.75 | 2.75 | 2.75 |
| Betaine | 2.00 | 2.00 | 2.00 | 2.00 | 2.00 | 2.00 |
| Behenyl Alcohol | 1.50 | 1.50 | 1.50 | 1.50 | 1.50 | 1.50 |
| Cetearyl Alcohol | 1.50 | 1.50 | 1.50 | 1.50 | 1.50 | 1.50 |
| Butylene Glycol | 0.95 | 0.95 | 0.95 | 0.95 | 0.95 | 0.95 |
| Aluminum Starch Octenylsuccinate | 0.93 | 0.93 | 0.93 | 0.93 | 0.93 | 0.93 |
| Dimethicone | 0.90 | 0.90 | 0.90 | 0.90 | 0.90 | 0.90 |
| Propylene Glycol | 0.77 | 0.77 | 0.77 | 0.77 | 0.77 | 0.77 |
| Arachidyl Glucoside | 0.75 | 0.75 | 0.75 | 0.75 | 0.75 | 0.75 |
| Panthenol | 0.60 | 0.60 | 0.60 | 0.60 | 0.60 | 0.60 |
| Carbomer | 0.30 | 0.30 | 0.30 | 0.30 | 0.30 | 0.30 |
| Fragrance | 0.23 | 0.23 | 0.23 | 0.23 | 0.23 | 0.23 |
| Sodium Acrylate/Sodium Acryloyldimethyl Taurate Copolymer | 0.15 | 0.15 | 0.15 | 0.15 | 0.15 | 0.15 |
| Ethyl Lauroyl Arginate*HCl | 0.40 | — | — | — | — | 0.40 |
| Piroctone Olamine | — | — | — | — | — | 1.00 |
| Sodium Sulfite | — | — | — | — | — | 0.20 |
| Hexetidine | — | 0.10 | 0.10 | — | — | 0.10 |
| Formic acid | 0.40 | — | — | — | — | 0.50 |
| Phenoxyisopropanol | — | — | — | — | — | 1.00 |
| Undecylenic acid | — | — | — | — | — | 0.20 |
| Chloroxylenol | — | — | 0.50 | — | — | 0.50 |
| Benzyl Alcohol | — | 1.00 | — | — | — | 1.00 |

-continued

| Raw material | 4.1 | 4.2 | 4.3 | 4.4 | 4.5 | 4.6 |
|---|---|---|---|---|---|---|
| Chlorphenesin | — | — | — | — | — | 0.30 |
| PM [1) ] | — | — | — | 0.1 | 1.0 | — |
| Polyisobutene | 0.11 | 0.11 | 0.11 | 0.11 | 0.11 | 0.11 |
| Yogurt | 0.10 | 0.10 | 0.10 | 0.10 | 0.10 | 0.10 |
| Allantoin | 0.10 | 0.10 | 0.10 | 0.10 | 0.10 | 0.10 |
| Bisabolol | 0.09 | 0.09 | 0.09 | 0.09 | 0.09 | 0.09 |
| Mentha Aquatica Leaf Extract | 0.03 | 0.03 | 0.03 | 0.03 | 0.03 | 0.03 |
| Sorbitol | 0.03 | 0.03 | 0.03 | 0.03 | 0.03 | 0.03 |
| Tocopherol | 0.03 | 0.03 | 0.03 | 0.03 | 0.03 | 0.03 |
| Hydrogenated Palm Glycerides Citrate | 0.02 | 0.02 | 0.02 | 0.02 | 0.02 | 0.02 |
| Sebacic Acid | 0.02 | 0.02 | 0.02 | 0.02 | 0.02 | 0.02 |
| 10-Hydroxydecanoic Acid | 0.02 | 0.02 | 0.02 | 0.02 | 0.02 | 0.02 |
| 1.10-Decanediol | 0.02 | 0.02 | 0.02 | 0.02 | 0.02 | 0.02 |
| Sorbitan Oleate | 0.01 | 0.01 | 0.01 | 0.01 | 0.01 | 0.01 |
| Caprylyl/Capryl Glucoside | 0.01 | 0.01 | 0.01 | 0.01 | 0.01 | 0.01 |
| Water | ad 100 | ad 100 | ad 100 | ad 100 | ad 100 | ad 100 |

[1)] Preservative mixture, selected from one of the previously specified preservative mixtures PM1 to PM157

20

Washing cream (values in % by weight)

| Raw material | 5.1 | 5.2 | 5.3 | 5.4 | 5.5 | 5.6 |
|---|---|---|---|---|---|---|
| Sodium Cocoyl Isethionate | 14.85 | 14.85 | 14.85 | 14.85 | 14.85 | 14.85 |
| Stearic Acid | 9.75 | 9.75 | 9.75 | 9.75 | 9.75 | 9.75 |
| Talc | 4.00 | 4.00 | 4.00 | 4.00 | 4.00 | 4.00 |
| Cocamidopropyl Betaine | 3.61 | 3.61 | 3.61 | 3.61 | 3.61 | 3.61 |
| Palmitic Acid | 3.00 | 3.00 | 3.00 | 3.00 | 3.00 | 3.00 |
| Zea Mays | 2.20 | 2.20 | 2.20 | 2.20 | 2.20 | 2.20 |
| Sodium Isethionate | 0.90 | 0.90 | 0.90 | 0.90 | 0.90 | 0.90 |
| Sodium Chloride | 0.67 | 0.67 | 0.67 | 0.67 | 0.67 | 0.67 |
| Fragrance | 0.60 | 0.60 | 0.60 | 0.60 | 0.60 | 0.60 |
| Ethyl Lauroyl Arginate*HCl | — | — | — | — | — | 0.40 |
| Piroctone Olamine | 0.50 | 0.50 | — | — | — | 1.00 |
| Sodium Sulfite | — | — | — | — | — | 0.20 |
| Hexetidine | — | 0.10 | 0.10 | — | — | 0.10 |
| Formic acid | — | — | — | — | — | 0.50 |
| Phenoxyisopropanol | 1.00 | — | — | — | — | 1.00 |
| Undecylenic acid | — | — | — | — | — | 0.20 |
| Chloroxylenol | — | — | — | — | — | 0.50 |
| Benzyl Alcohol | — | — | — | — | — | 1.00 |
| Chlorphenesin | — | — | 0.30 | — | — | 0.30 |
| PM [1)] | — | — | — | 0.3 | 1.2 | — |
| Propylene Glycol | 0.28 | 0.28 | 0.28 | 0.28 | 0.28 | 0.28 |
| Citric Acid | 0.20 | 0.20 | 0.20 | 0.20 | 0.20 | 0.20 |
| Mannitol | 0.11 | 0.11 | 0.11 | 0.11 | 0.11 | 0.11 |
| Tetrasodium EDTA | 0.04 | 0.04 | 0.04 | 0.04 | 0.04 | 0.04 |
| Tocopherol | 0.03 | 0.03 | 0.03 | 0.03 | 0.03 | 0.03 |
| Hydrogenated Palm Glycerides Citrate | 0.02 | 0.02 | 0.02 | 0.02 | 0.02 | 0.02 |
| Camellia Sinensis Leaf Extract | 0.01 | 0.01 | 0.01 | 0.01 | 0.01 | 0.01 |
| Water | ad 100 | ad 100 | ad 100 | ad 100 | ad 100 | ad 100 |

[1)] Preservative mixture, selected from one of the previously specified preservative mixtures PM1 to PM157

Shower gel (values in % by weight)

| Raw material | 6.1 | 6.2 | 6.3 | 6.4 | 6.5 | 6.6 |
|---|---|---|---|---|---|---|
| Sodium Laureth Sulfate | 9.10 | 9.10 | 9.10 | 9.10 | 9.10 | 9.10 |
| Cocamidopropyl Betaine | 1.90 | 1.90 | 1.90 | 1.90 | 1.90 | 1.90 |
| Sodium Chloride | 1.35 | 1.35 | 1.35 | 1.35 | 1.35 | 1.35 |
| Glycerin | 1.00 | 1.00 | 1.00 | 1.00 | 1.00 | 1.00 |
| Fragrance | 0.67 | 0.67 | 0.67 | 0.67 | 0.67 | 0.67 |
| PEG-7 Glyceryl Cocoate | 0.40 | 0.40 | 0.40 | 0.40 | 0.40 | 0.40 |
| Coco-Glucoside | 1.00 | 1.00 | 1.00 | 1.00 | 1.00 | 1.00 |
| Styrene/Acrylates Copolymer | 0.30 | 0.30 | 0.30 | 0.30 | 0.30 | 0.30 |
| Citric Acid | 0.27 | 0.27 | 0.27 | 0.27 | 0.27 | 0.27 |
| Laureth-2 | 0.25 | 0.25 | 0.25 | 0.25 | 0.25 | 0.25 |
| Ethyl Lauroyl Arginate*HCl | — | — | 0.40 | — | — | 0.40 |
| Piroctone Olamine | — | — | — | — | — | 1.00 |
| Sodium Sulfite | — | — | — | — | — | 0.20 |

-continued

| Raw material | 6.1 | 6.2 | 6.3 | 6.4 | 6.5 | 6.6 |
|---|---|---|---|---|---|---|
| Hexetidine | — | 0.10 | 0.10 | — | — | 0.10 |
| Formic acid | 0.50 | 0.50 | — | — | — | 0.50 |
| Phenoxyisopropanol | 1.00 | — | — | — | — | 1.00 |
| Undecylenic acid | — | — | — | — | — | 0.20 |
| Chloroxylenol | — | — | — | — | — | 0.50 |
| Benzyl Alcohol | — | — | — | — | — | 1.00 |
| Chlorphenesin | — | — | — | — | — | 0.30 |
| PM [1] | — | — | — | 0.9 | 0.25 | — |
| Caprylyl/Capryl Glucoside | 0.14 | 0.14 | 0.14 | 0.14 | 0.14 | 0.14 |
| Polyquaternium-7 | 0.14 | 0.14 | 0.14 | 0.14 | 0.14 | 0.14 |
| Propylene Glycol | 0.10 | 0.10 | 0.10 | 0.10 | 0.10 | 0.10 |
| PEG-55 Propylene Glycol Oleate | 0.10 | 0.10 | 0.10 | 0.10 | 0.10 | 0.10 |
| Water | 83.04 | 83.04 | 83.04 | 83.04 | 83.04 | 83.04 |

[1] Preservative mixture, selected from one of the previously specified preservative mixtures PM1 to PM157

Cleaning agent (values in % by weight)

| Raw material | 7.1 | 7.2 | 7.3 | 7.4 | 7.5 | 7.6 |
|---|---|---|---|---|---|---|
| Disodium Laureth Sulfosuccinate | 10.00 | 10.00 | 10.00 | 10.00 | 10.00 | 10.00 |
| PEG-7 Glyceryl Cocoate | 3.50 | 3.50 | 3.50 | 3.50 | 3.50 | 3.50 |
| Capryl/Capramidopropyl Betaine | 1.40 | 1.40 | 1.40 | 1.40 | 1.40 | 1.40 |
| Propylene Glycol | 1.08 | 1.08 | 1.08 | 1.08 | 1.08 | 1.08 |
| Decyl Glucoside | 1.06 | 1.06 | 1.06 | 1.06 | 1.06 | 1.06 |
| Glycerin | 0.86 | 0.86 | 0.86 | 0.86 | 0.86 | 0.86 |
| Coco-Glucoside | 0.85 | 0.85 | 0.85 | 0.85 | 0.85 | 0.85 |
| Glyceryl Oleate | 0.73 | 0.73 | 0.73 | 0.73 | 0.73 | 0.73 |
| Sorbitol | 0.70 | 0.70 | 0.70 | 0.70 | 0.70 | 0.70 |
| Sodium PCA | 0.50 | 0.50 | 0.50 | 0.50 | 0.50 | 0.50 |
| Fragrance | 0.41 | 0.41 | 0.41 | 0.41 | 0.41 | 0.41 |
| Ethyl Lauroyl Arginate*HCl | — | — | — | — | — | 0.40 |
| Piroctone Olamine | 0.5 | — | — | — | — | 1.00 |
| Sodium Sulfite | — | — | 0.20 | — | — | 0.20 |
| Hexetidine | — | — | — | — | — | 0.10 |
| Formic acid | — | — | — | — | — | 0.50 |
| Phenoxyisopropanol | 1.00 | — | — | — | — | 1.00 |
| Undecylenic acid | — | — | — | — | — | 0.20 |
| Chloroxylenol | — | 0.50 | — | — | — | 0.50 |
| Benzyl Alcohol | — | 1.00 | — | — | — | 1.00 |
| Chlorphenesin | — | — | 0.30 | — | — | 0.30 |
| PM [1] | — | — | — | 0.7 | 0.01 | — |
| Lactic Acid | 0.36 | 0.36 | 0.36 | 0.36 | 0.36 | 0.36 |
| Sodium Chloride | 0.30 | 0.30 | 0.30 | 0.30 | 0.30 | 0.30 |
| Sodium Lactate | 0.12 | 0.12 | 0.12 | 0.12 | 0.12 | 0.12 |
| Tetrasodium EDTA | 0.10 | 0.10 | 0.10 | 0.10 | 0.10 | 0.10 |
| Citric Acid | 0.08 | 0.08 | 0.08 | 0.08 | 0.08 | 0.08 |
| Persea Gratissima Oil | 0.03 | 0.03 | 0.03 | 0.03 | 0.03 | 0.03 |
| Tocopherol | 0.03 | 0.03 | 0.03 | 0.03 | 0.03 | 0.03 |
| Hydrogenated Palm Glycerides Citrate | 0.02 | 0.02 | 0.02 | 0.02 | 0.02 | 0.02 |
| Persea Gratissima Oil Unsaponifables | 0.02 | 0.02 | 0.02 | 0.02 | 0.02 | 0.02 |
| Prunus Amygdalus Dulcis Oil | 0.02 | 0.02 | 0.02 | 0.02 | 0.02 | 0.02 |
| Water | 76.97 | 76.97 | 76.97 | 76.97 | 76.97 | 76.97 |

[1] Preservative mixture, selected from one of the previously specified preservative mixtures PM1 to PM157

Face toner (values in % by weight)

| Raw material | 8.1 | 8.2 | 8.3 | 8.4 | 8.5 | 8.6 |
|---|---|---|---|---|---|---|
| Mentha Piperita Water | 2.99 | 2.99 | 2.99 | 2.99 | 2.99 | 2.99 |
| Glycerin | 2.10 | 2.10 | 2.10 | 2.10 | 2.10 | 2.10 |
| Cocamidopropyl Betaine | 0.57 | 0.57 | 0.57 | 0.57 | 0.57 | 0.57 |
| Ethyl Lauroyl Arginate*HCl | — | — | 0.40 | — | — | 0.40 |
| Piroctone Olamine | 1.0 | — | — | — | — | 1.00 |
| Sodium Sulfite | — | — | — | — | — | 0.20 |
| Hexetidine | 0.1 | 0.10 | — | — | — | 0.10 |
| Formic acid | — | — | — | — | — | 0.50 |
| Phenoxyisopropanol | — | — | — | — | — | 1.00 |
| Undecylenic acid | — | 0.20 | 0.20 | — | — | 0.20 |

-continued

| Raw material | 8.1 | 8.2 | 8.3 | 8.4 | 8.5 | 8.6 |
|---|---|---|---|---|---|---|
| Chloroxylenol | — | — | — | — | — | 0.50 |
| Benzyl Alcohol | — | — | — | — | — | 1.00 |
| Chlorphenesin | — | — | — | — | — | 0.30 |
| PM [1] | — | — | — | 1.8 | 0.09 | — |
| Tilia Platyphyllos Flower Water | 0.45 | 0.45 | 0.45 | 0.45 | 0.45 | 0.45 |
| Sodium Chloride | 0.11 | 0.11 | 0.11 | 0.11 | 0.11 | 0.11 |
| Citric Acid | 0.10 | 0.10 | 0.10 | 0.10 | 0.10 | 0.10 |
| Water | ad 100 | ad 100 | ad 100 | ad 100 | ad 100 | ad 100 |

[1] Preservative mixture, selected from one of the previously specified preservative mixtures PM1 to PM157

Shower cream (values in % by weight)

| Raw material | 9.1 | 9.2 | 9.3 | 9.4 | 9.5 | 9.6 |
|---|---|---|---|---|---|---|
| Sodium Laureth Sulfate | 9.50 | 9.50 | 9.50 | 9.50 | 9.50 | 9.50 |
| Disodium Cocoamphodiacetate | 1.56 | 1.56 | 1.56 | 1.56 | 1.56 | 1.56 |
| Cocamidopropyl Betaine | 1.52 | 1.52 | 1.52 | 1.52 | 1.52 | 1.52 |
| Sodium Chloride | 1.38 | 1.38 | 1.38 | 1.38 | 1.38 | 1.38 |
| Fragrance | 0.62 | 0.62 | 0.62 | 0.62 | 0.62 | 0.62 |
| Glycol Distearate | 0.45 | 0.45 | 0.45 | 0.45 | 0.45 | 0.45 |
| Citric Acid | 0.37 | 0.37 | 0.37 | 0.37 | 0.37 | 0.37 |
| PEG-7 Glyceryl Cocoate | 0.30 | 0.30 | 0.30 | 0.30 | 0.30 | 0.30 |
| Cocamide MEA | 0.23 | 0.23 | 0.23 | 0.23 | 0.23 | 0.23 |
| Ethyl Lauroyl Arginate*HCl | — | 0.40 | — | — | — | 0.40 |
| Piroctone Olamine | — | — | — | — | — | 1.00 |
| Sodium Sulfite | — | — | 0.20 | — | — | 0.20 |
| Hexetidine | — | — | — | — | — | 0.10 |
| Formic acid | — | — | 0.50 | — | — | 0.50 |
| Phenoxyisopropanol | 1.0 | — | — | — | — | 1.00 |
| Undecylenic acid | — | — | 0.20 | — | — | 0.20 |
| Chloroxylenol | 0.50 | — | — | — | — | 0.50 |
| Benzyl Alcohol | — | — | — | — | — | 1.00 |
| Chlorphenesin | — | 0.30 | — | — | — | 0.30 |
| PM [1] | — | — | — | 0.001 | 0.4 | — |
| PEG-40 Hydrogenated Castor Oil | 0.20 | 0.20 | 0.20 | 0.20 | 0.20 | 0.20 |
| Polyquaternium-7 | 0.14 | 0.14 | 0.14 | 0.14 | 0.14 | 0.14 |
| Laureth-10 | 0.09 | 0.09 | 0.09 | 0.09 | 0.09 | 0.09 |
| Laureth-2 | 0.05 | 0.05 | 0.05 | 0.05 | 0.05 | 0.05 |
| Propylene Glycol | 0.02 | 0.02 | 0.02 | 0.02 | 0.02 | 0.02 |
| PEG-55 Propylene Glycol Oleate | 0.02 | 0.02 | 0.02 | 0.02 | 0.02 | 0.02 |
| Water | ad 100 | ad 100 | ad 100 | ad 100 | ad 100 | ad 100 |

[1] Preservative mixture, selected from one of the previously specified preservative mixtures PM1 to PM157

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cleaning composition, including, in a cosmetically acceptable carrier,
   a) at least one surfactant selected from the group consisting of anionic surfactants, cationic surfactants, amphoteric surfactants, non-ionic surfactants, and mixtures thereof, and
   b) at least one preservative mixture, selected from the group consisting of
      phenoxyisopropanol and formic acid,
      sulfite(s) and hexetidine,
      ethyl lauroyl arginate and formic acid,
      ethyl lauroyl arginate and chloroxylenol,
      hexetidine and benzyl alcohol,
      hexetidine and chloroxylenol,
      hexetidine and formic acid,
      and mixtures thereof, and
   c) further including at least two further preservatives, each selected from the group consisting of benzyl alcohol(s), undecylenic acid, formic acid, piroctone olamine, sulfite(s), hexetidine, ethyl lauroyl arginate, and chlorphenesin, with the provision that the cleaning composition includes at least 4 different preservatives.

2. The cleaning composition according to claim 1, wherein the at least one surfactant is included at a concentration of 0.5 to 60% by weight, based on the total weight of the cleaning composition.

3. The cleaning composition according to claim 1, wherein the at least one surfactant includes at least one anionic surfactant selected from the group consisting of (i) alkyl(ether) sulfate having 8 to 18 carbon atoms in the alkyl chain and 1 to 6 ethylene oxide units, (ii) $C_{12}$-$C_{18}$ alkylether carboxylates, (iii) $C_{12}$-$C_{18}$ acyl isethionates, (iv) $C_{12}$-$C_{18}$ acyl sarcosinates, (v) $C_{12}$-$C_{18}$ acyl taurines, and (vi) mixtures thereof.

4. The cleaning composition according to claim 1, wherein the at least one surfactant includes at least one cationic surfactant selected from the group consisting of (i) quaternized carboxylic acid triethanolamine ester salts, (ii) quaternized salts of carboxylic acids with diethanol alkylamines, (iii) quaternized salts of carboxylic acids with 1,2-dihydroxypropyldialkylamines, (iv) Quaternium-92, (v) $C_{10}$-$C_{22}$ alkyltrimethylammonium chlorides, and (vi) mixtures thereof.

5. The cleaning compositions according to claim 1, wherein the at least one surfactant includes at least one amphoteric surfactant selected from the group consisting of (i) $C_{10}$-$C_{18}$ alkyl betaines, (ii) $C_{8-12}$-alkylamido($C_{1-4}$)-alkyl betaines, (iii) $C_{10}$-$C_{18}$ alkyl sulfobetaines, (iv) $C_{10}$-$C_{18}$ alkyl amphoacetates and amphodiacetates, (v) $C_{10}$-$C_{18}$ alkylamphopropionates and dipropionates, and (vi) mixtures thereof.

6. The cleaning composition according to claim 1, wherein the at least one surfactant includes at least one non-ionic surfactant selected from the group consisting of (i) $C_{10}$-$C_{18}$ alkyl polyglucosides, (ii) sorbitan esters and sorbitan ether esters, (iii) $C_{10}$-$C_{18}$ carboxylic acid monoethanol amides, (iv) $C_{10}$-$C_{18}$ alcohol ethoxylates with 2 to 40 mol ethylene oxide and/or propylene oxide per mol of alcohol, (v) $C_{10}$-$C_{18}$ amine oxides, (vi) glyceryl cocoates with 2 to 40 mol ethylene oxide and/or propylene oxide per mol of glyceryl cocoate, and (vii) mixtures thereof.

7. The cleaning composition according to claim 1, wherein the at least one preservative combination b) is included at a concentration of 0.001 to 10% by weight based on the total weight of the cleaning composition.

8. The cleaning composition according to claim 1, wherein a ratio by weight of the first preservative to the second preservative in the preservative mixture b) is from 10:1 to 1:10.

9. The cleaning composition according to claim 1, further including at least three further preservatives, each selected from the group consisting of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 5 different preservatives.

10. The cleaning composition according to claim 1, further including at least four further preservatives, each selected from the group consisting of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 6 different preservatives.

11. The cleaning composition according to claim 1, further including at least six further preservatives, each selected from the group consisting of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 8 different preservatives.

12. The cleaning composition according to claim 1, wherein the at least two additional preservatives are is included at a concentration of 0.1 to 10% by weight relative to the total weight of the cleaning composition.

13. A method for preservation of surfactant-containing cleaning compositions, including
a) providing at least one preservative mixture in the cleaning composition, the at least one preservative mixture being selected from the group consisting of phenoxyisopropanol and formic acid, sulfite(s) and hexetidine, ethyl lauroyl arginate and formic acid, ethyl lauroyl arginate and chloroxylenol, hexetidine and benzyl alcohol, hexetidine and chloroxylenol, hexetidine and formic acid, and mixtures thereof,
b) further including at least two further preservatives, each selected from the group consisting of benzyl alcohol(s), undecylenic acid, formic acid, piroctone olamine, sulfite(s), hexetidine, ethyl lauroyl arginate, and chlorphenesin, with the provision that the cleaning composition includes at least 4 different preservatives.

14. A cleansing composition, in a cosmetically acceptable carrier, comprising
at least one surfactant, selected from the group consisting of anionic surfactants, cationic surfactants, amphoteric surfactants, nonionic surfactants, and mixtures thereof, and
a combination of preservatives consisting of:
a first preservative mixture selected from the group consisting of
phenoxyisopropanol and piroctone olamine,
phenoxyisopropanol and formic acid,
sulfite(s) and hexetidine,
ethyl lauroyl arginate and formic acid,
ethyl lauroyl arginate and chloroxylenol,
hexetidine and benzyl alcohol,
hexetidine and chloroxylenol,
hexetidine and piroctone olamine,
hexetidine and chlorophenesin,
hexetidine and formic acid, and mixtures thereof and further including at least two further preservatives, each selected from the group consisting of benzyl alcohol(s), chloroxylenol, phenoxyisopropanol, undecylenic acid, formic acid, piroctone olamine, sulfite(s), hexetidine, ethyl lauroyl arginate, and chlorphenesin, with the provision that the cleaning composition includes at least 4 different preservatives.

* * * * *